(12) United States Patent
Ellis et al.

(10) Patent No.: US 9,101,372 B2
(45) Date of Patent: *Aug. 11, 2015

(54) DEVICE AND METHOD FOR USE DURING LIGAMENT RECONSTRUCTION SURGERY

(71) Applicant: Smith & Nephew, Inc., Andover, MA (US)

(72) Inventors: Daniel B Ellis, Holliston, MA (US); Michael C. Ferragamo, Foster, RI (US); Bryce BederkaP, Portland, OR (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/215,624

(22) Filed: Mar. 17, 2014

(65) Prior Publication Data

US 2014/0200585 A1    Jul. 17, 2014

Related U.S. Application Data

(63) Continuation of application No. 12/397,454, filed on Mar. 4, 2009, now Pat. No. 8,734,461.

(60) Provisional application No. 61/033,648, filed on Mar. 4, 2008.

(51) Int. Cl.
| | | |
|---|---|---|
| *A61B 17/56* | (2006.01) |
| *A61B 17/17* | (2006.01) |
| *A61B 17/88* | (2006.01) |
| *A61F 2/08* | (2006.01) |
| *A61B 5/107* | (2006.01) |
| *A61B 19/00* | (2006.01) |

(52) U.S. Cl.
CPC ............ *A61B 17/1764* (2013.01); *A61B 5/1076* (2013.01); *A61B 17/8897* (2013.01); *A61F 2/0805* (2013.01); *A61B 17/1714* (2013.01); *A61B 2019/462* (2013.01); *A61B 2019/547* (2013.01)

(58) Field of Classification Search
CPC ............ A61B 5/1076; A61B 17/1714; A61B 17/1764; A61B 17/8897; A61B 2019/462; A61B 2019/547; A61B 2/0805
USPC .............. 606/86 R, 87, 96, 99, 102, 104, 232
See application file for complete search history.

(56) References Cited

U.S. PATENT DOCUMENTS

| | | |
|---|---|---|
| 5,180,388 A | 1/1993 | DiCarlo |
| 5,549,613 A | 8/1996 | Goble |
| 5,645,588 A | 7/1997 | Graf et al. |
| 5,891,150 A | 4/1999 | Chan |
| 5,931,840 A | 8/1999 | Goble |
| 6,120,511 A | 9/2000 | Chan |

(Continued)

FOREIGN PATENT DOCUMENTS

| | | |
|---|---|---|
| EP | 0 463 551 A1 | 1/1992 |
| EP | 0556570 A1 | 8/1993 |

(Continued)

*Primary Examiner* — Larry E Waggle, Jr.
(74) *Attorney, Agent, or Firm* — Chapin IP Law, LLC

(57) ABSTRACT

The present disclosure relates to a device for use in ligament reconstruction surgery. The device includes a handle, a tube coupled to the handle, and a locking mechanism coupled to the handle. A method for use during ligament reconstruction surgery is also disclosed.

9 Claims, 6 Drawing Sheets

(56) References Cited

U.S. PATENT DOCUMENTS

| | | |
|---|---|---|
| 6,162,226 A | 12/2000 | DeCarlo |
| 7,131,974 B2 | 11/2006 | Keyer et al. |
| 7,175,633 B2 | 2/2007 | Roth et al. |
| 8,070,750 B2 | 12/2011 | Wenstrom et al. |
| 8,177,841 B2 | 5/2012 | Ek |
| 8,308,662 B2 | 11/2012 | Lo |
| 8,734,461 B2 * | 5/2014 | Ellis et al. ............ 606/96 |
| 8,870,891 B2 * | 10/2014 | Lizardi et al. .......... 606/102 |
| 2002/0133165 A1 | 9/2002 | Whittaker et al. |
| 2004/0092936 A1 | 5/2004 | Miller et al. |
| 2008/0188935 A1 | 8/2008 | Saylor et al. |

FOREIGN PATENT DOCUMENTS

| | | |
|---|---|---|
| JP | 2000333964 | 5/2000 |
| WO | 9415556 A1 | 7/1994 |
| WO | 2005122921 A2 | 12/2005 |

\* cited by examiner

DEVICE AND METHOD FOR USE DURING LIGAMENT RECONSTRUCTION SURGERY

CROSS-REFERENCE TO RELATED APPLICATIONS

This application claims priority to U.S. patent application Ser. No. 12/397,454, filed Mar. 4, 2009 and claims the benefit of U.S. Provisional Application No. 61/033,648, filed Mar. 4, 2008, the disclosure of which is incorporated herein by reference in its entirety.

BACKGROUND

1. Field of Technology

The present disclosure relates to ligament reconstruction surgery, and more specifically, a device and method for determining lengths during reconstruction surgery.

2. Related Art

The creation of reconstruction tunnels in the femur for ligament reconstruction surgery is required for the attachment of a soft tissue graft, such as a patellar tendon or a semitendinosis tendon. The lengths of the femoral tunnels needs to be determined and calculations need to be made to determine the appropriate lengths for the implants that are used to fixate the grafts in the tunnels. Currently, manual calculations are used to determine these lengths. These manual calculations are often inaccurate and time consuming. Therefore, a device and method for calculating these lengths are needed.

SUMMARY

In one aspect, the present disclosure relates to a device for use in ligament reconstruction surgery. The device includes a handle, a tube coupled to the handle, and a locking mechanism coupled to the handle. The handle includes a first set of markings, a second set of markings, and a window located between the first and second set of markings. The tube is cannulated and includes a first end portion coupled to the handle and a second end portion. The locking mechanism includes a shaft and a knob coupled to the shaft.

In another aspect, the present disclosure relates to a method for use during ligament reconstruction surgery. The method includes providing a device including a handle, the handle including a first set of markings, a second set of markings, and a window located between the first and second set of markings, a cannulated tube coupled to the handle, the tube including a first end and a second end, and a locking mechanism coupled to the handle, the locking mechanism including a shaft and a knob coupled to the shaft; providing a guide wire, the guide wire having a first end portion including an opening, a second end portion including markings, and a laser mark located between the first and second end; inserting the guide wire through a tibia and femur such that the second end portion extends from the femur; inserting the tube of the device over the second end portion of the guide wire until the first end of the tube abuts a surface of the femur; correlating the second end portion of the guide wire with a marking from the first set of markings to determine a desired length for a femoral tunnel; and correlating a marking on the second end portion of the guide wire with a marking on the second set of markings to determine a desired length for an implant suture. The method may further include drilling tunnels through the tibia and the femur; coupling suture to the first end of the guide wire; coupling the suture to a tissue graft; and inserting the tissue graft into the tunnels via use of the guide wire.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
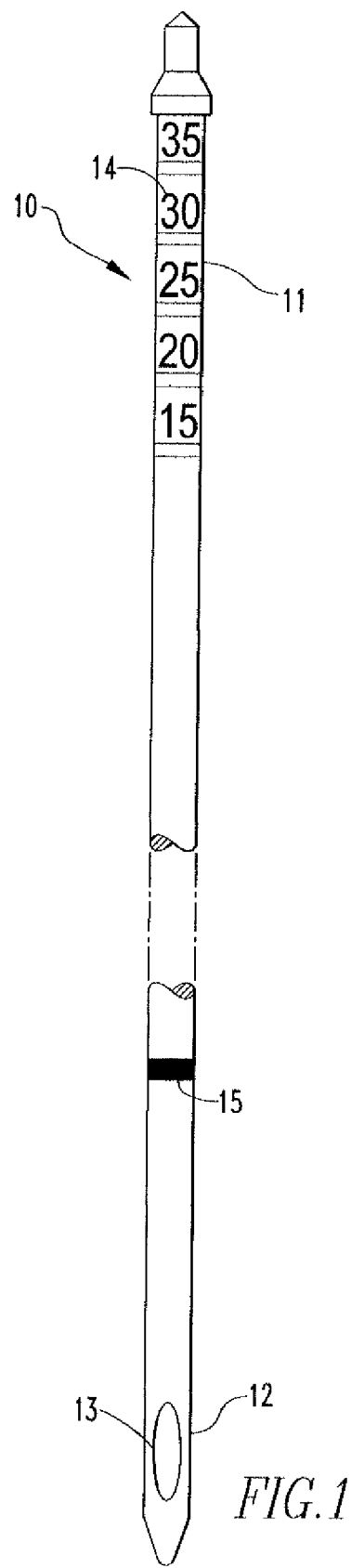
FIG. 1 shows a guide wire of the present disclosure.

FIG. 1 shows a guide wire 10 having a first end portion 11 and a second end portion 12. The second end portion 12 includes an opening 13 and the first end portion 11 includes number markings 14. The guide wire 10 also includes a laser mark 15 located along a length of the guide wire 10. The laser mark 15 serves as a reference point for calculations that are taken in preparation for a ligament reconstruction procedure, as will be further described below. For the purposes of this disclosure, the laser mark 15 is in the shape of a ring that extends the entire diameter of the guide wire 10. However, the shape and the number of laser marks may vary. For instance, instead of having one laser mark that is in the shape of a ring, two laser marks may exist that are located 180° from each other or more than two laser marks may exist with the laser marks forming a discontinuous ring that extends the entire diameter of the guide wire 10.

Figure 2:
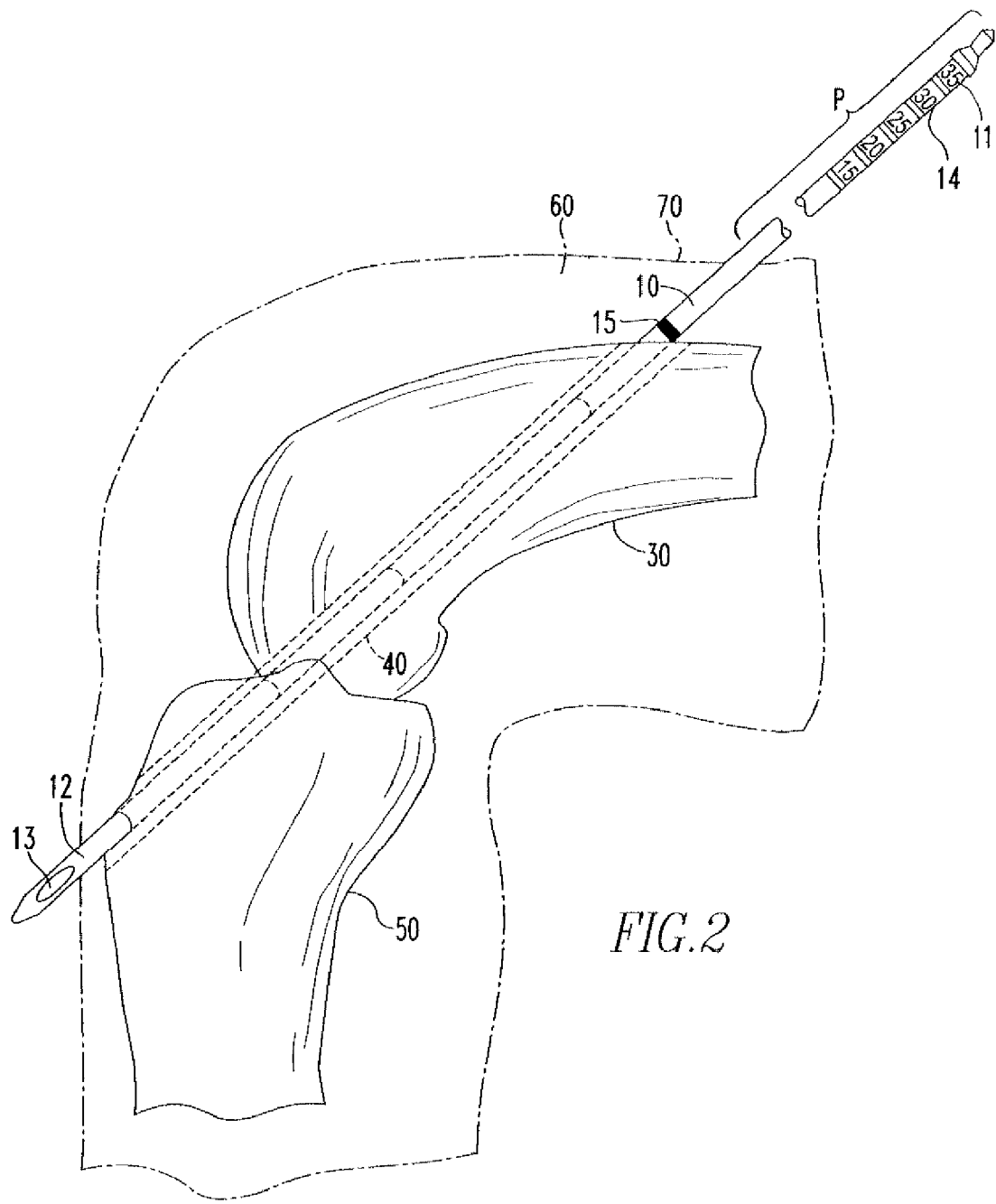
FIG. 2 shows the guide wire of FIG. 1 inserted through a desired bone tunnel path of a knee joint.

During reconstruction surgery, the knee joint is viewed arthroscopically to determine proper positioning of the femoral and tibial tunnels. In addition, guide systems may be used to position a drill guide along the desired tunnel paths prior to drilling of the tunnels. An example of a guide system is described in U.S. Pat. No. 5,139,520, the disclosure of which is incorporated herein by reference in its entirety. In the present disclosure, after proper positioning of the tunnels has been determined, the guide wire 10 is drilled along the desired tunnel path 40, through the tibia 50, the femur 30, and the quadriceps 60 and skin 70, as shown in FIG. 2, such that a portion P of the guide wire 10 extends through the skin 70. As mentioned above, the laser mark serves as a reference point for subsequent calculations. Generally, when inserting the guide 10 through the knee joint, the surgeon will align the laser mark 15 with the outer surface, or cortical layer, of the femur 30, as shown in FIG. 2. The laser mark 15 represents 0 mm on the guide wire 10 and the markings 14 represent a certain distance from the laser mark 15.

Figure 3:
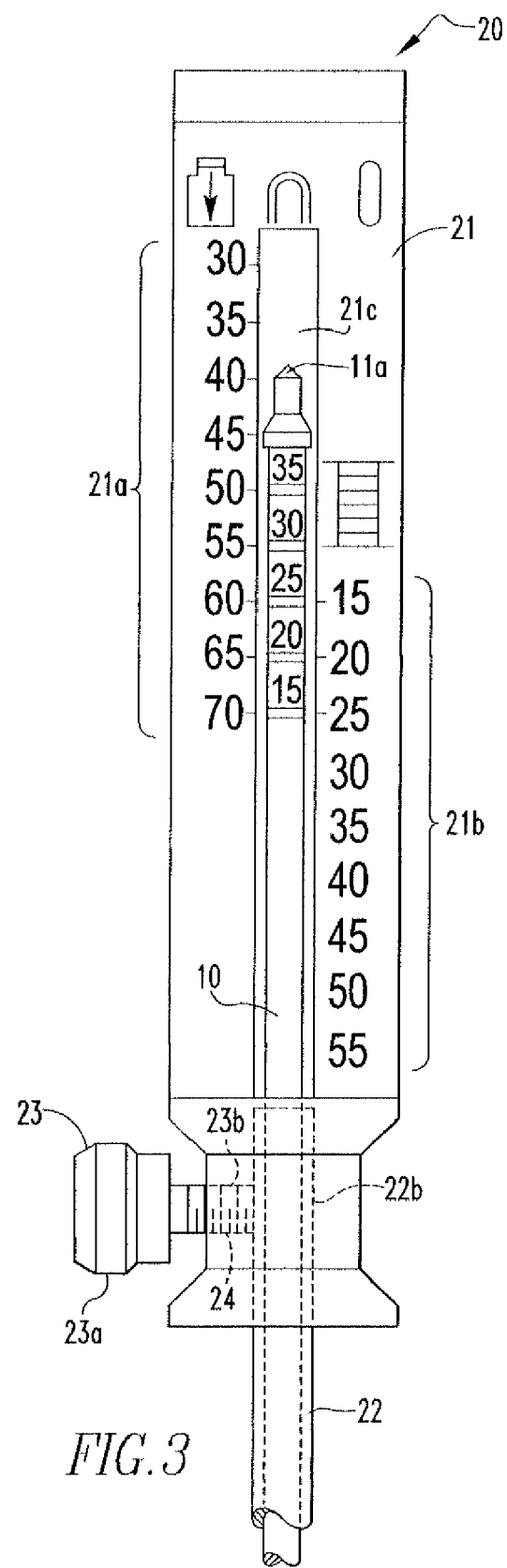
FIGS. 3 and 4 show the guide wire of FIG. 1 disposed within the device for use in ligament reconstruction surgery of the present disclosure.
Figure 4:
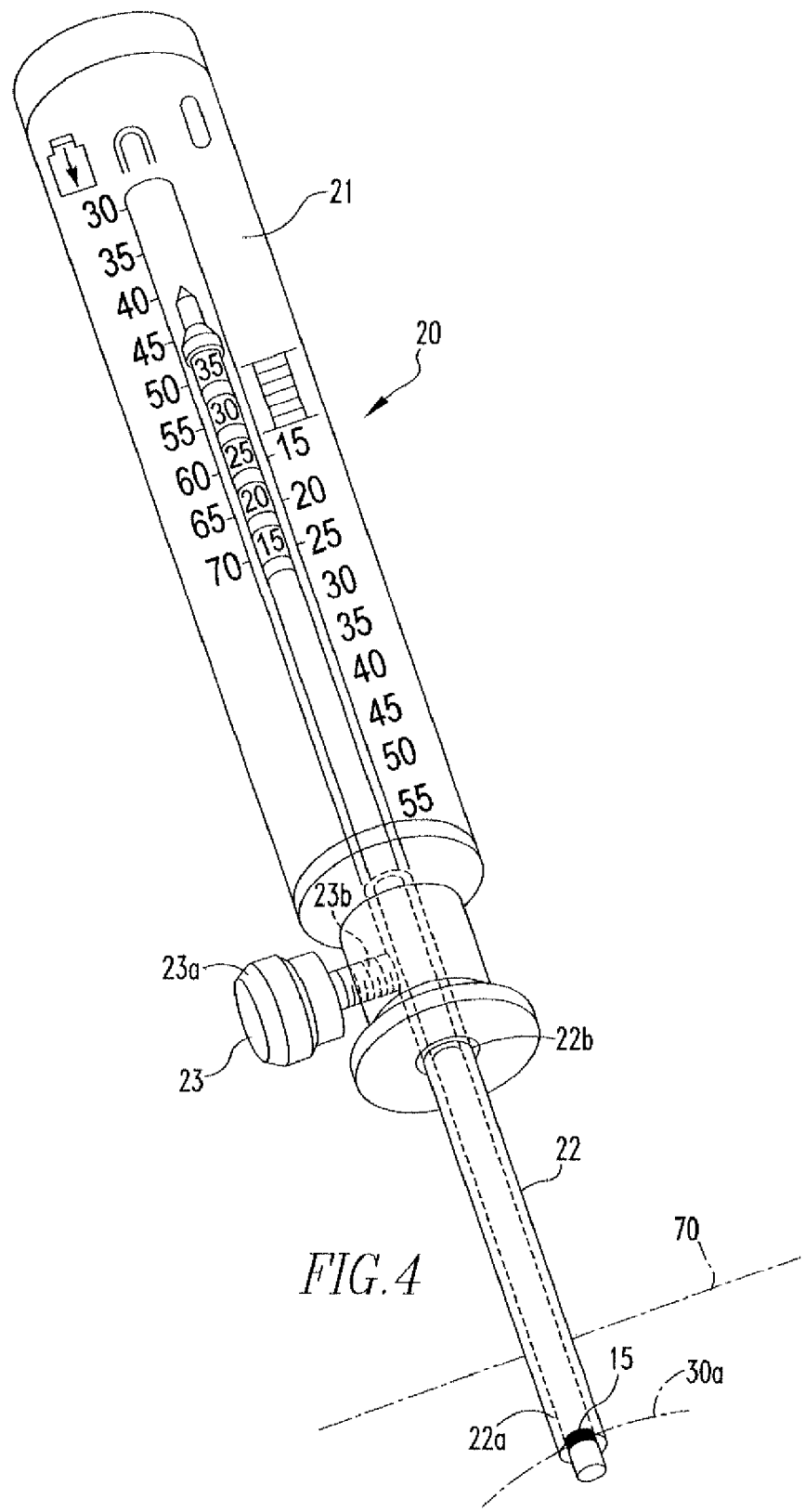

A device 20, as shown in FIGS. 3 and 4, is then placed over the portion P of the guide wire 10 extending through the skin 70. The device 20 includes a handle 21, a tube 22 having a first end 22a and a second end 22b, and a locking mechanism 23 coupled to the handle 21. The locking mechanism 23 includes a knob 23a and a shaft 23b coupled to the knob 23a. The shaft 23b is located in a through hole 24 that extends through the handle 21 and the tube 22. The device 20 is placed over the guide wire portion P such that the first end 22a of the tube 22 extends through the skin and rests against the femoral cortex 30a, as shown in FIG. 4. Once the end 22a is resting against the femoral cortex 30a, the knob 23a is rotated to engage the guide wire 10 and fixate the guide wire 10 to the device 20. The handle 21 of the device 20 includes markings 21a, 21b and a window 21c for viewing portion P of the guide wire 10. The first end portion 11 of the guide wire 10, specifically the tip 11a of the second end portion 11, correlates with markings 21a to provide a calculation of the depth of the desired femoral tunnel. The depth will vary based on the trajectory or angle, relative to the tibia and femur, at which the guide 10 is inserted through the knee joint and the physical size of the bone. In the example shown in FIG. 3, the depth of the tunnel is 40 mm.

Next, the surgeon finds the appropriate marking 14 on the guide wire 10 that corresponds to the length of a tissue graft that will be used to replace the damaged ligament. A tissue graft, such as a patellar tendon or a semitendonosis tendon, is harvested from the femur and measured, prior to the guide wire being placed into the joint, via harvesting and measurement techniques known to one of ordinary skill in the art. The markings 14 on the guide wire 10 correspond to markings 21b to provide a size calculation for the suture loop that will be used in connection with a fixation device and suture to couple the graft to the second end 12 of the guide wire 10, as will be further described below. For example, as can be seen in FIG. 3, if the length of the tissue graft is 20 mm, then the length of the suture loop should be 20 mm. The length of the suture loop will also vary based on the trajectory or angle, relative to the tibia and femur, at which the guide 10 is inserted through the knee joint and the physical size of the bone. Examples of a suture loop and fixation device that may be used are described in U.S. Pat. Nos. 5,306,301 and 6,533,802, the disclosures of which are incorporated herein by reference in their entirety.

Figure 5:
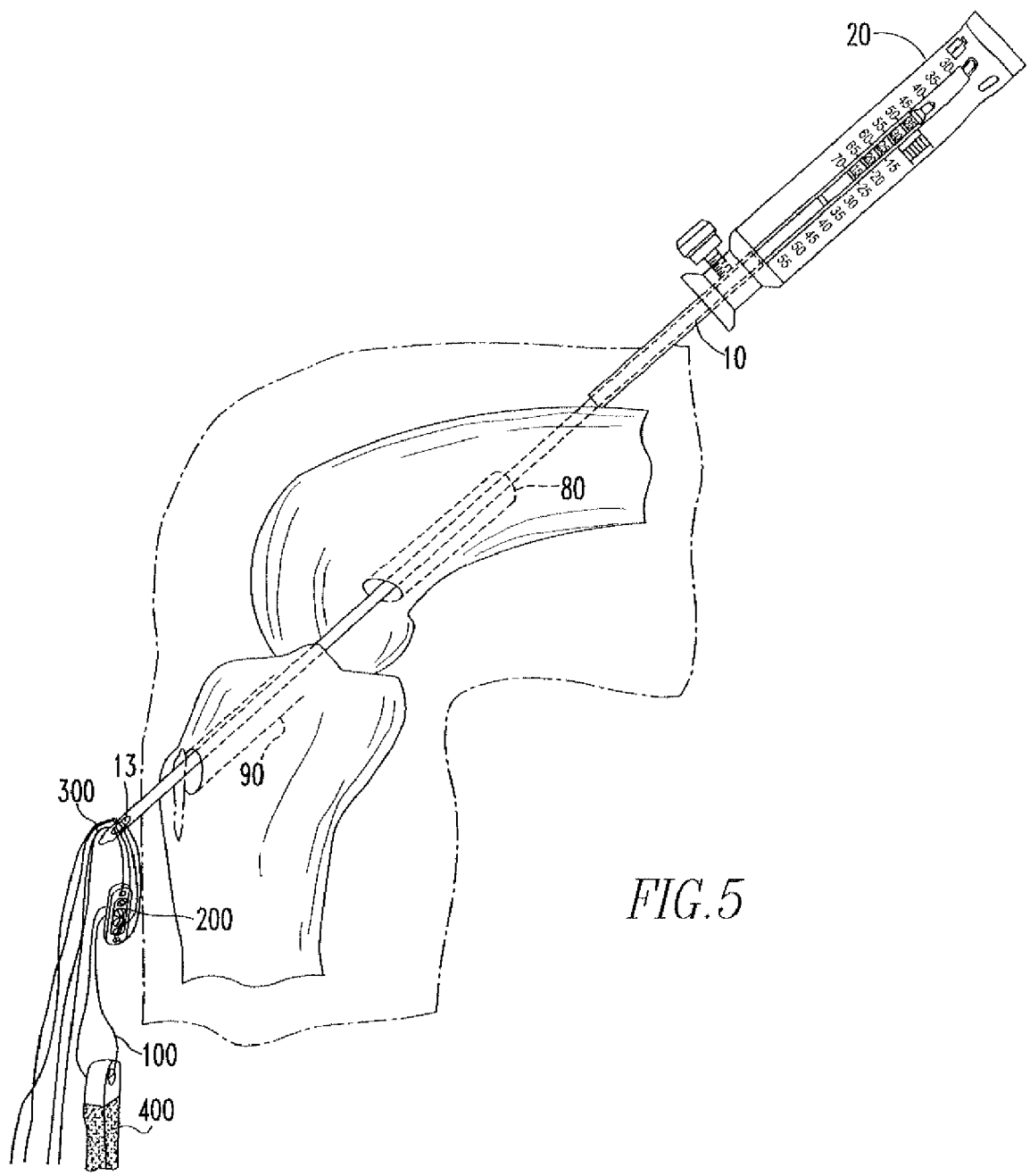
FIG. 5 shows the device and the guide wire of the present disclosure in use during ligament reconstruction surgery.
Figure 6:
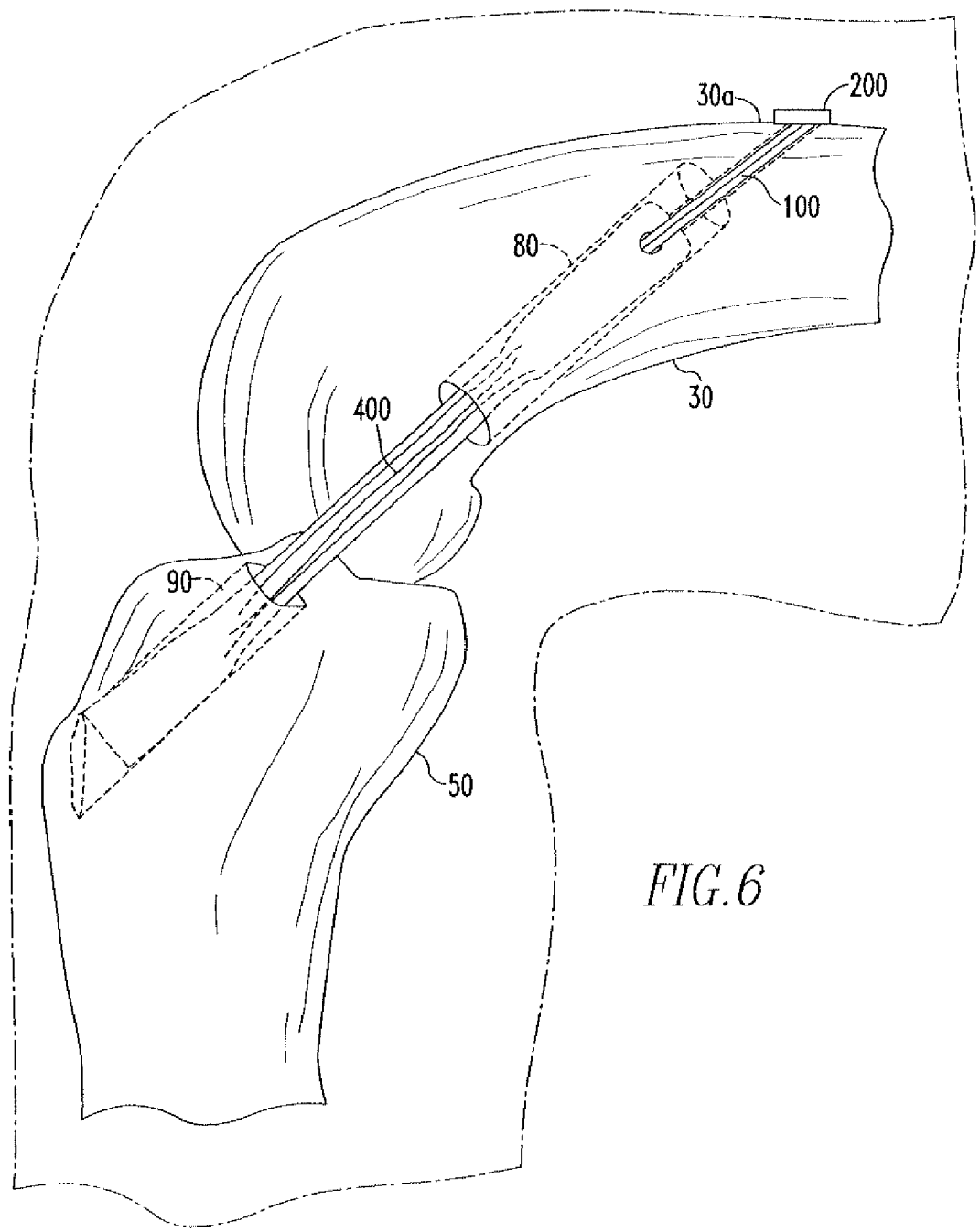
FIG. 6 shows a soft tissue graft fixated with femoral and tibial bone tunnels.

After a calculation of the desired tunnel and suture loop length has been determined, drilling of the femoral and tibial tunnels occurs, via drilling techniques known to one of ordinary skill in the art, using the guide wire 10 as a drilling guide. As can be seen in FIG. 5, after drilling of the femoral and tibial tunnels 80,90, suture 300 is passed through the opening 13 of the guide wire 10 and then coupled to the graft 400, via the fixation device 200 to couple the guide wire 10 to the graft 400. The fixation device 200 is previously coupled to the graft 400 via the suture loop 100. The surgeon may then use the device 20 to pull the graft 400 into the tunnels 80,90 and the fixation device 200 onto the femoral cortex 30a, as shown in FIG. 6. Coupling of the suture 300 and the graft 400 to the fixation device 200 may occur as described in the '301 and '802 patents identified above.

The guide wire 10 includes a biocompatible metal material, such as stainless material or titanium alloy. The opening 13 and the markings 14 on the first and second end portions 11,12 of the guide wire 10 may be made via a punch press or other machining or engraving process. The handle 21, tube 22, and knob 23a also include a biocompatible metal material, such as stainless steel or titanium alloy, and may be made from a molding or machining process. The first and second set of markings 21a, 21b may be made by a machining or engraving process. The shaft 23b may be threaded and the through hole 24 may have matching threading to facilitate movement of the shaft through the through hole 24 as the shaft 23b is rotated.

The device 20 of the present disclosure allows for calculation of the femoral tunnel length and uses a formula for determining the appropriate suture loop size based on the graft length that is selected by the surgeon, thereby eliminating the need to perform manual calculations. In addition, the device can be used to safely remove the guide wire from the tibial and femoral tunnels.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A device for use in ligament reconstruction surgery comprising:
   a handle comprising a first set of markings, a second set of markings, and a window located between the first and second set of markings, the second set of markings corresponding to a size of a suture loop for use with a bone tunnel;
   a tube coupled to the handle such that a second end of the tube is directly attached to a hole of the handle, the window providing visibility to guidewire markings on a guidewire disposed through the tube and the hole.

2. The device of claim 1 wherein the tube is cannulated and receptive to the guidewire when passed therethrough.

3. The device of claim 1 wherein the first set of markings is indicative of a depth of a femoral tunnel based on alignment of a tip of the guidewire with the first set of markings.

4. The device of claim 1 wherein the second set of markings is indicative of a size of a suture loop based on alignment of the second set of markings with the guidewire markings.

5. The device of claim 1 wherein the guidewire markings are indicative of a length of a suture graft corresponding to the aligned suture loop size.

6. The device of claim 1 wherein the window provides visibility to guidewire markings relative to the first set of markings.

7. The device of claim 1 wherein the first set of markings corresponds to an insertion depth for determining a depth of the guidewire based a distance to a first end of the tube.

8. The device of claim 7 wherein the first set of markings determines depth based on a distance to a cortical region of a femur of a patient.

9. The device of claim 1, wherein the depth is determined relative to a lasermark on the guidewire, the lasermark disposed at the outer surface of a cortical layer.

* * * * *